United States Patent
Balder

(10) Patent No.: US 9,994,884 B2
(45) Date of Patent: Jun. 12, 2018

(54) PROCESSES AND METHODS OF MANUFACTURE OF ARECOLINE

(71) Applicant: Vapor Corp, Dania Beach, FL (US)

(72) Inventor: Edwin Balder, Mesa, AZ (US)

(73) Assignee: Healthier Choices Management Corp., Hollywood, FL (US)

( * ) Notice: Subject to any disclaimer, the term of this patent is extended or adjusted under 35 U.S.C. 154(b) by 108 days.

(21) Appl. No.: 15/272,211

(22) Filed: Sep. 21, 2016

(65) Prior Publication Data

US 2017/0009264 A1     Jan. 12, 2017

Related U.S. Application Data

(63) Continuation-in-part of application No. 13/999,650, filed on Mar. 15, 2014, now Pat. No. 9,526,270.

(51) Int. Cl.
| | |
|---|---|
| *C12P 17/12* | (2006.01) |
| *A24B 15/30* | (2006.01) |
| *A24B 15/16* | (2006.01) |
| *A61K 31/455* | (2006.01) |
| *A61K 36/889* | (2006.01) |
| *A23L 25/00* | (2016.01) |

(52) U.S. Cl.
CPC ............... *C12P 17/12* (2013.01); *A23L 25/30* (2016.08); *A24B 15/16* (2013.01); *A24B 15/167* (2016.11); *A61K 31/455* (2013.01); *A61K 36/889* (2013.01); *A61K 2236/13* (2013.01); *A61K 2236/15* (2013.01); *A61K 2236/19* (2013.01); *A61K 2236/51* (2013.01)

(58) Field of Classification Search
None
See application file for complete search history.

(56) References Cited

U.S. PATENT DOCUMENTS

| 7,291,352 B2 * | 11/2007 | Gow ............... A61K 31/366 424/725 |
| 7,381,434 B2 | 6/2008 | Gow et al. |
| 2005/0053678 A1 | 3/2005 | Gow et al. |

FOREIGN PATENT DOCUMENTS

| CN | 1019124496 A | | 12/2010 |
| CN | 102464607 A | | 5/2012 |
| CN | 104957336 A | * | 10/2015 |
| WO | WO 2004/068974 A1 | * | 8/2004 |

OTHER PUBLICATIONS

Machine translation of CN 104957336, The European Patent Office, [online], [retrieved on Jul. 15, 2016]. Retrieved from the Internet: <URL: http://ep.espacenet.com/?locale=EN_ep>.*
Machine Translation of CN101912496A, Google Patents, 4 pages, retrieved from the Internet, [retrieved Sep. 16, 2016], URL:http://googlepatents.com.
Machine Translation of CN102464607A, Google Patents, 3 pages, retrieved from the Internet, [retrieved Sep. 16, 2016], URL:http://googlepatents.com.

* cited by examiner

*Primary Examiner* — Dennis R Cordray
(74) *Attorney, Agent, or Firm* — Lewis Brisbois Bisgaard & Smith LLP; Geoffrey Lottenberg, Esq.

(57) ABSTRACT

Processes and methods of manufacturing an areca fruit product. One process may include the steps of providing a plurality of areca fruits, drying the plurality of areca fruits, dehusking the plurality of areca fruits to obtain a plurality of areca nuts, chopping, shredding or grinding the plurality of areca nuts into a multiplicity of areca nut particles, introducing the multiplicity of areca nut particles into a tank containing water, agitating the multiplicity of areca nut particles to create a slurry, determining an amount of arecoline in the slurry and pumping the water having the predetermined amount of arecoline through a filter and into a holding tank and concentrating the arecoline in an evaporator. Additional steps include fermentation, distillation, pasteurization, and cold pressing of the arecoline to produce a synthetic nicotine and/or botanical pesticide.

7 Claims, No Drawings

PROCESSES AND METHODS OF MANUFACTURE OF ARECOLINE

CROSS REFERENCE TO RELATED APPLICATIONS

This application is a continuation-in-part of U.S. application Ser. No. 13/999,650, dated Mar. 15, 2014, which claims priority to U.S. Provisional Application Ser. No. 61/852,401, filed Mar. 15, 2013.

DETAILED DESCRIPTION OF THE INVENTION

In the following description, for the purposes of explanation, numerous specific details are set forth in order to provide a thorough understanding of the synthetic or imitation nicotine of the present invention. It will be apparent, however, to one skilled in the art that the synthetic or imitation nicotine may be practiced without some of these specific details. Throughout this description, the embodiments and examples shown should be considered as exemplars, rather than as limitations on the synthetic or imitation nicotine. That is, the following description provides examples, and the accompanying drawings show various examples for the purposes of illustration. However, these examples should not be construed in a limiting sense as they are merely intended to provide examples of the synthetic or imitation nicotine rather than to provide an exhaustive list of all possible implementations of the synthetic or imitation nicotine.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner in one or more embodiments.

The social taboo of smoking nicotine-containing products like cigarettes, cigars, pipes and the like continues to increase. However, individuals may wish to continue to enjoy nicotine. The present invention provides compositions, mixtures, and methods of manufacture for a synthetic or imitation nicotine. Embodiments of the present invention provide tobacco flavor, and/or transmit nicotine or other medical preparations that add to the enrichment and/or safety of vapor passing through the mouthpiece end of an electric (or other power source), cigarette, electric cigar, or any vaporizing apparatus.

Generally, nicotinic receptors are integral membrane proteins that respond specifically to receptors involved in the regulation of a variety of physiological and behavioral functions including memory, cognition, respiration, concentration etc. Such correlations suggest that nicotine and its analogs which modulate nicotinic acetylcholine receptors that are mimicked into our synthetic or imitation nicotine will have beneficial effects for discouraging the urge to use nicotine.

Though only certain types of these receptors are associated with addiction, nicotine activates all of them non-selectively and may cause dependency after long term use. However, nicotine's well-known potential for abuse and toxic effects on the gastrointestinal and cardiovascular systems prevent its use as a drug. Development of a synthetic or imitation compound based on the core nicotine structure, without these side effects, has been limited by the lack of methods for preparing synthetic or imitation derivatives from naturally available nicotine. Thus, there is a need to develop methods for synthesis of nicotine analogs with receptor-type selectivity for safe and effective replacement of nicotine.

One nicotine analog that may he employed by the present invention comprises arecoline, an alkaloid found in the areca nut (also known as betel nut), the fruit of the areca palm (Areca catechu). The areca nuts contain at least nine (9) structurally related pyridine alkaloids, including arecoline, arecaidine, arecaine, arecolidine, guvacine, isoguvacine, guvacoline, and coniine However, the most common is the parasympathetic stimulant alkaloid arecoline. The total alkaloid content can reach 0.45%.

The areca palm grows in much of the tropical Pacific, Asia, and parts of east Africa. It is commonly referred to as betel nut, as it is often chewed wrapped in betel leaves. The areca nut is not a true nut, but rather a drupe. It is commercially available in dried, cured and fresh forms. While fresh, the husk is green and the nut inside is soft enough to be cut with a typical knife. In the ripe fruit, the husk becomes yellow or orange and, as it dries, the fruit inside hardens to a wood-like consistency. Usually consumed by chewing, a few slices of the nut are wrapped in a betel leaf along with lime (not to be confused with the citrus fruit named lime) and may include clove, cardamom, catechu (kattha) and/or other spices for extra flavoring. Betel leaf has a fresh, peppery taste, but it can also be bitter to varying degrees depending on the variety.

Arecoline is a strong base, with pKa—6.8. Arecoline is volatile in steam, miscible with most organic solvents and water, but extractable from the latter by ether in presence of dissolved salts. Being basic, arecoline forms salts with acids. The salts are crystalline, but usually deliquescent: the hydrochloride, arecoline-CI; the hydrobromide, arecoline-Br; and the urichloride, arecoline-AuC14.

Arecoline is the primary active ingredient responsible for the central nervous system effects of the areca nut. Arecoline has been compared to nicotine; however, nicotine acts primarily on the nicotinic acetylcholine receptor. Arecoline is known to be a partial agonist of uscarinic acetylcholine M1, M2, M3 receptors and M4, which is believed to be the primary cause of its parasympathetic effects (such as pupillary constriction, bronchial constriction, etc.). These central nervous system effects on humans may also have analogous functions in insects and other pests whereby the arecoline can function as a natural botanical pesticide.

Basic ingredients employed in the arecoline product of the present invention may be used alone or in combination with other additives are distilled or manipulated to insure conformity to health standards. These ingredients can be applied after extracting from organics n a solid, powder or liquid form in a concentrate or a tincture, oil or in another base.

Embodiments of the present invention comprise novel processes that involve producing synthetic or imitation nicotine from naturally occurring chemical compounds, such as arecoline. Other substances contained include, but are not limited to: vegetable-glycol (VG), lycerin, polyglycol (PG), tannin, gallic acid, nipecotic acid, a fixed oil gum, terpineol, lignin, various saline substances and up to five (5) alkaloids.

For example, one method of practicing the present invention comprises a process of preparing an areca fruit, the process comprising the steps of providing a plurality of areca fruits, drying the plurality of areca fruits, dehusking the plurality of areca fruits to obtain a purality of areca nuts, chopping, shredding or grinding the plurality of areca nuts into a multiplicity of areca nut particles, with a mean particle size of between 300-5000 microns, immersing the multiplicity of areca nut particles in a water filled tank to create a slurry and extracting an arecoline from the slurry.

The slurry is recycled through the water filled tank as additional multiplicities of areca nut particles are added to the water filled tank until an arecoline concentration in the water reaches a predetermined amount and pumping the water having the predetermined amount of arecoline through a filter and into a holding tank. The water having the predetermined amount of arecoline is transferred from the holding tank into an evaporator and the arecoline is concentrated in the evaporator. The concentrated arecoline is transferred to a spray drier, and the arecoline is collected from the spray drier in a dry powder form.

One embodiment of imitation nicotine of the present invention comprises evaporating the arecoline to a solid content that may range between 10% and 90%, but other percentages may also be employed. The arecoline is mixed with another element which may be any one of: an alcohol, a water, a vegetable glycol, a glycerin, a poly-glycol, and a combination of two or more thereof.

Another method of practicing the present invention comprises a process of preparing an areca fruit, the process comprising the steps of providing a plurality of areca fruits, drying the plurality of areca fruits, dehusking the plurality of areca fruits to obtain a plurality of areca nuts, chopping, shredding or grinding the plurality of areca nuts into a multiplicity of areca nut particles, introducing the multiplicity of areca nut particles into a tank containing a mixture comprising water at a temperature between 40-90° Centigrade and a pH adjusted to a range between 4.0 and 8.0, and adding at least one element, the element selected from a group consisting of: a sulfuric acid, a salt, an organic solvent, an ether, and a combination of two or more thereof. The mixture is then agitated to create a slurry, and an amount, or percentage of arecoline in the slurry is determined. Additional multiplicities of areca nut particles may be added to the tank until an arecoline concentration in the tank reaches a desired amount and then the water having the predetermined amount of arecoline is pumped through a filter that removes all, or most of the areca nut particles. The water is then introduced to an evaporator that concentrates the arecoline. If necessary, a spray drier may also be employed until the arecoline is in a dry powder form. Once in a dry powder from, the arecoline may be used in an imitation nicotine product of the present invention.

In other embodiments, one method of practicing the present invention comprises a process of preparing an areca fruit, the process comprising the steps of providing a plurality of areca fruits, drying the plurality of areca fruits, dehusking the plurality of areca fruits to obtain a purality of areca nuts, chopping, shredding or grinding the plurality of areca nuts into a multiplicity of areca nut particles, with an exemplary mean particle size of between 300-5000 microns, immersing the multiplicity of areca nut particles in a water filled tank to create a slurry. Extraction and preparation of arecoline may be accomplished by methods complimentary to or in substitution for the evaporation/concentration methods heretofore disclosed, for example, methods of fermentation, pasteurization, distillation, and/or cold pressing processes may be employed to obtain a final arecoline product.

Fermentation can be included into this process and can be carried out in a variety of ways inside a sealed container that has qualities that allow for the expulsion of gasses that may develop, but all methods depend on placing the slurry in a solution, for example a water-based solution, that allow micro-organisms to develop and initiate the fermentation. The process requires growth of micro-organisms where products like yeasts are added to the slurry. The yeasts convert any sugars present in the arecoline slurry to produce ethanol. Complex chemical changes take place with the slurry producing a reaction of breakdown of proteins, enzyme activity, and/or oxidation resulting in amino acids. Following fermentation of the arecoline slurry, nonessential elements of the resultant fermented arecoline is filter to obtain a purer final product. In some embodiment, the fermentation step can occur after the concentration step in the above methods, whereby concentrated arecoline is reprocessed into a slurry and later fermented. This allows the desired quantities and final quality of the arecoline product to be specified more readily.

A pasteurization process may also be put into operation at slurry stage or as a secondary step following concentration of the arecoline as described above. The process of pasteurization is accomplished by increasing the temperature of the slurry solution high enough to destroy or significantly reduce the number of viable pathogens, such as bacteria, so they are unlikely to cause disease and inactivate most enzymes that cause spoilage. This can be done in temperature safe containers where the temperature can be safely increased to the current level required to establish pasteurization. Pasteurization methods are usually standardized and controlled by national food safety agencies but most require that the slurry is heated to at least 72° C. for at least 16 seconds then cooling it to 4° C. to ensure any harmful bacteria are destroyed. Pasteurization can greatly increase the sterility and shelf-life of the resultant arecoline product, providing a safer and more marketable final product.

Distillation of the slurry can also be added as step at the slurry stage or as a secondary step following concentration of arecoline. In some embodiments, the slurry or concentrated arecoline is purified by precipitating and collecting the hot vapors coming off the boiling slurry or re-wetted arecoline solution are collected. Both atmospheric and vacuum distillation methods can be employed but vacuum methods are particularly useful after distilling the slurry at atmospheric pressure. Vacuum distallation requires a lower boiling point that thereby eliminates heat that could facilitate unwanted chemical reactions within the arecoline slurry or concentrate or that would otherwise combust useful and active elements of the arecoline.

Cold pressing of the slurry or the concentrated arecoline can also be incorporated as an additional method step. Cold pressing offers the advantage of eliminating heat and producing a concentrate that has been filtered while being pressed. The slurry or arecoline concentrate is placed into an industrial filter bag and then is compressed allowing the particulate matter to be eliminated resulting in a cold-pressed areca fruit product or concentrated pressed product free from organic solids. This product has a more uniform resultant product that can be incorporated into admixtures and formulated for uses where it is undesirable to have solid particulate matter.

The arecoline final product produce in accordance with the various embodiments of the present methodology may be mixed with another element, the element selected from a group consisting of: an alcohol, a water, a vegetable glycol, a glycerin, a poly-glycol, and a combination of two or more thereof. This mixture may be sprayed on a material and the material may be flavored with a tobacco or a menthol flavor. Alternatively, the mixture may be kept in a liquid form and used in an electronic cigarette, vaporizer or other apparatus.

That is, the imitation nicotine can be delivered in a powder or liquid form with varying percentages of active base obtained by addition or subtraction of non-active organics or matter. Potency can be easily regulated by volume. When the arecoline is distilled to a 16% level of concentration or more and added to vegetable-glycol (VG) or, glycerin or poly-glycol (PG), this tincture mixture can produce a working imitation nicotine product that can be used in electric vapor units. Any desired concentration of volatile aroma/flavor in a smoking material may be controlled by adjusting concentrations of the solutions or by adjusting spray or coating rates. Process solvents, where they are used, are preferably evaporated from the smoking material prior to further treatment. The advantage of applying the volatile aroma/flavor components before addition of the other components of the smoking materials is that good fixation and stabilization results. The volatiles absorbed onto or into the fibrous structures of the smoking material are effectively encapsulated by succeeding layers of components deposited upon them.

Propylene glycol, which may be used in the present invention, also called 1,2-propanediol or propane-1,2-diol, is an organic compound (a diol or double alcohol) with formula $C_3H_8O_2$. It is a colorless, nearly odorless, clear, viscous liquid with a faintly sweet taste, hygroscopic and miscible with water, acetone, and chloroform. The commercial product is a racemic mixture. Propylene glycol is considered generally recognized as safe (GRAS) by the U.S. Food and Drug Administration, and it is used as an humectant (E1520), solvent, and preservative in food and for tobacco products, as well as being one of the major ingredients in "e-liquid" used in electronic cigarettes along with vegetable glycerin. Propylene glycol is also used in the vapor used in vaporizers.

The acute oral toxicity of propylene glycol is very low, and large quantities are required to cause perceptible health damage in humans; propylene glycol is metabolized in the human body into pyruvic acid (a normal part of the glucose-metabolism process, readily converted to energy), acetic acid (handled by ethanol-metabolism), lactic acid (a normal acid generally abundant during digestion), and propionaldehyde (a potentially hazardous substance). Serious toxicity generally occurs only at plasma concentrations over 1 g/L, which requires extremely high intake over a relatively short period of time. It would be nearly impossible to reach toxic levels by consuming foods or supplements, which contain at most 1 g/kg of propylene glycol. The potential for long-term oral toxicity is also low. Because of its low chronic oral toxicity, propylene glycol was classified by the U. S. Food and Drug Administration as "generally recognized as safe" (GRAS) for use as a direct food additive.

Glycerol (or glycerine, glycerin) is a simple polyol (sugar alcohol) compound, which may also be employed by the present invention. It is a colorless, odorless, viscous liquid that is widely used in pharmaceutical formulations. Glycerol has three hydroxyl groups that are responsible for its solubility in water and its hygroscopic nature. The glycerol backbone is central to all lipids known as triglycerides. Glycerol is sweet-tasting and of low toxicity. In food and beverages, glycerol serves as a humectant, solvent, and sweetener, and may help preserve foods. It is also used as filler in commercially prepared low-fat foods (e.g., cookies), and as a thickening agent in liqueurs. Glycerol and water are used to preserve certain types of leaves. As a sugar substitute, it has approximately 27 kilocalories per teaspoon (sugar has 20) and is 60% as sweet as sucrose. It does not feed the bacteria that form plaques and cause dental cavities. As a food additive, glycerol is labeled as E number E422. It is added to icing (frosting) to prevent it setting too hard.

As used in foods, glycerol is categorized by the American Dietetic Association as a carbohydrate. The U.S. Food and Drug Administration (FDA) carbohydrate designation includes all caloric macronutrients excluding protein and fat. Glycerol has a caloric density similar to table sugar, but a lower glycemic index and different metabolic pathway within the body, so some dietary advocates accept glycerol as a sweetener compatible with low carbohydrate diets.

The present invention may modulate nicotinic acetylcholine receptors and other systems that cause nicotine addiction and hence, comprises a potential therapeutic for several nicotine related addictions, symptoms or disorders. In addition to arecoline, other compounds may be employed, such as C-4 substituted; alkyl or aryl substituted; halogenated; C-4 and C-5 substituted halogenated synthetic or imitation nicotine analogs. Many of these novel compounds have demonstrated high receptor selectivity during testing making them good candidates for development to replace nicotine in any and all applications that formally contained nicotine or in the future might contain nicotine, including but not limited to, smoking, vaporizing or any application derived from tobacco.

Some of the advantages of the present invention include compounds that have therapeutic value to help remove withdrawal symptoms from nicotine use and analogs that have medicinal benefits of nicotine without its side-effects. The present invention utilizes commercially available and inexpensive raw material, and the process for preparing the analogs is efficient and amenable to large scale production.

The terms "including", "comprising" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise. None of the description in the present application should be read as implying that any particular element, step, or function is an essential element which must be included in the claim scope. The scope of the patented subject matter is defined only by the allowed claims. Moreover, none of these claims are intended to invoke paragraph six of 35 USC Section 112 unless the exact words "means' for" are followed by a participle.

Thus, it is seen that compositions, processes and methods of manufacturing synthetic or imitation nicotine are provided. However it is appreciated an understood that the present methods and processes can be utilized to produce an arecoline final product with uses beyond a nicotine substitute, such uses including but not limited to as a natural botanical pesticide and fertilizer.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that many alternatives, modifications, permutations and variations will become apparent to those of ordinary skill in the art in light of the foregoing description.

What is claimed is:

1. A process of preparing an areca fruit product, the process comprising the steps of:
   providing a plurality of areca fruits;
   drying the plurality of areca fruits;
   dehusking the plurality of areca fruits to obtain a plurality of areca nuts;
   chopping, shredding or grinding the plurality of areca nuts into a multiplicity of areca nut particles;
   introducing the multiplicity of areca nut particles into a tank containing water at a temperature between 40-90° Centigrade;
   agitating the multiplicity of areca nut particles to create a slurry;
   determining an amount of arecoline in the slurry;
   adding additional multiplicities of areca nut particles to the slurry until the slurry contains a predetermined amount of arecoline;
   pumping the slurry containing the predetermined amount of arecoline through a filter and into a holding tank; and
   fermenting said slurry containing the predetermined amount of arecoline by adding one or more microorganisms to said slurry.

2. The process of claim 1, further comprising the step of:
   before said fermenting step, transferring the slurry from the holding tank into an evaporator and concentrating the arecoline from the slurry in the evaporator.

3. A process of preparing an areca fruit product, the process comprising the steps of:
   providing a plurality of areca fruits;
   drying the plurality of areca fruits;
   dehusking the plurality of areca fruits to obtain a plurality of areca nuts;
   chopping, shredding or grinding the plurality of areca nuts into a multiplicity of areca nut particles;
   introducing the multiplicity of areca nut particles into a tank containing water at a temperature between 40-90° Centigrade;
   agitating the multiplicity of areca nut particles to create a slurry;
   determining an amount of arecoline in the slurry;
   adding additional multiplicities of areca nut particles to the slurry until the slurry contains a predetermined amount of arecoline;
   pumping the slurry containing the predetermined amount of arecoline through a filter and into a holding tank; and
   pasteurizing said slurry containing the predetermined amount of arecoline by first increasing the temperature of said slurry containing the predetermined amount of arecoline and then rapidly reducing the temperature of said slurry containing the predetermined amount of arecoline.

4. The process of claim 3, further comprising the step of:
   before said pasteurizing step, transferring the slurry from the holding tank into an evaporator and concentrating the arecoline from the slurry in the evaporator.

5. A process of preparing an areca fruit product, the process comprising the steps of:
   providing a plurality of areca fruits;
   drying the plurality of areca fruits;
   dehusking the plurality of areca fruits to obtain a plurality of areca nuts;
   chopping, shredding or grinding the plurality of areca nuts into a multiplicity of areca nut particles;
   introducing the multiplicity of areca nut particles into a tank containing water at a temperature between 40-90° Centigrade;
   agitating the multiplicity of areca nut particles to create a slurry;
   determining an amount of arecoline in the slurry;
   adding additional multiplicities of areca nut particles to the slurry until the slurry contains a predetermined amount of arecoline;
   pumping the slurry containing the predetermined amount of arecoline through a filter and into a holding tank;
   transferring the slurry from the holding tank into an evaporator;
   concentrating the arecoline from the slurry in the evaporator; and
   cold pressing said concentrated arecoline to extract said areca fruit product from said concentrated arecoline.

6. A process of preparing an areca fruit product, the process comprising the steps of:
   providing a plurality of areca fruits;
   drying the plurality of areca fruits;
   dehusking the plurality of areca fruits to obtain a plurality of areca nuts;
   chopping, shredding or grinding the plurality of areca nuts into a multiplicity of areca nut particles;
   introducing the multiplicity of areca nut particles into a tank containing water at a temperature between 40-90° Centigrade;
   agitating the multiplicity of areca nut particles to create a slurry;
   determining an amount of arecoline in the slurry;
   adding additional multiplicities of areca nut particles to the slurry until the slurry contains a predetermined amount of arecoline;
   pumping the slurry containing the predetermined amount of arecoline through a filter and into a holding tank; and
   vacuum distilling said slurry containing the predetermined amount of arecoline.

7. The process of claim 6, further comprising the step of:
   before said vacuum distilling step, transferring the slurry from the holding tank into an evaporator and concentrating the arecoline from the slurry in the evaporator.

* * * * *